United States Patent [19]

Gordon et al.

[11] 4,324,236

[45] Apr. 13, 1982

[54] FITTING FOR USE IN PERFORMING A VASCULAR PUNCTURE

[75] Inventors: Marvin Gordon, East Windsor; Joseph Lichtenstein, Cononia, both of N.J.

[73] Assignee: Whitman Medical Corp., Clark, N.J.

[21] Appl. No.: 99,926

[22] Filed: Dec. 3, 1979

[51] Int. Cl.³ .............................................. D61M 5/00
[52] U.S. Cl. ......................... 128/214 R; 128/DIG. 26
[58] Field of Search ..................... 128/214, 214.4, 348, 128/349, 133, 221, DIG. 26, DIG. 16, 346

[56] References Cited

U.S. PATENT DOCUMENTS

| | | | |
|---|---|---|---|
| 2,725,058 | 11/1955 | Rathkey | 128/221 |
| 3,064,648 | 11/1962 | Bujan | 128/214 R |
| 3,430,300 | 3/1969 | Doan | 128/DIG. 26 |
| 3,630,195 | 12/1971 | Santomieri | 128/133 |
| 3,782,383 | 1/1974 | Thompson et al. | 128/214 |
| 3,834,380 | 9/1974 | Boyd | 128/133 |
| 3,885,560 | 5/1975 | Baldwin | 128/214 R |
| 3,973,765 | 8/1976 | Steer | 128/214.4 |

*Primary Examiner*—Stephen C. Pellegrino
*Attorney, Agent, or Firm*—Holman & Stern

[57] ABSTRACT

A fitting for use in performing a vascular puncture includes a system for rapidly and securely stabilizing an intravascular catheter or needle to a patient's skin upon insertion of the needle or catheter into a blood vessel. The hub of the needle or catheter has upper and lower lateral wings extending from its opposite sides. The wings are folded up over the hub and gripped together while a vascular puncture is made and then the lower wings, which have adhesive under surfaces, are released and dabbed onto the skin to rapidly stabilize the fitting. The upper wings can be taped down over the lower wings to effect a more permanent attachment of the fitting.

11 Claims, 9 Drawing Figures

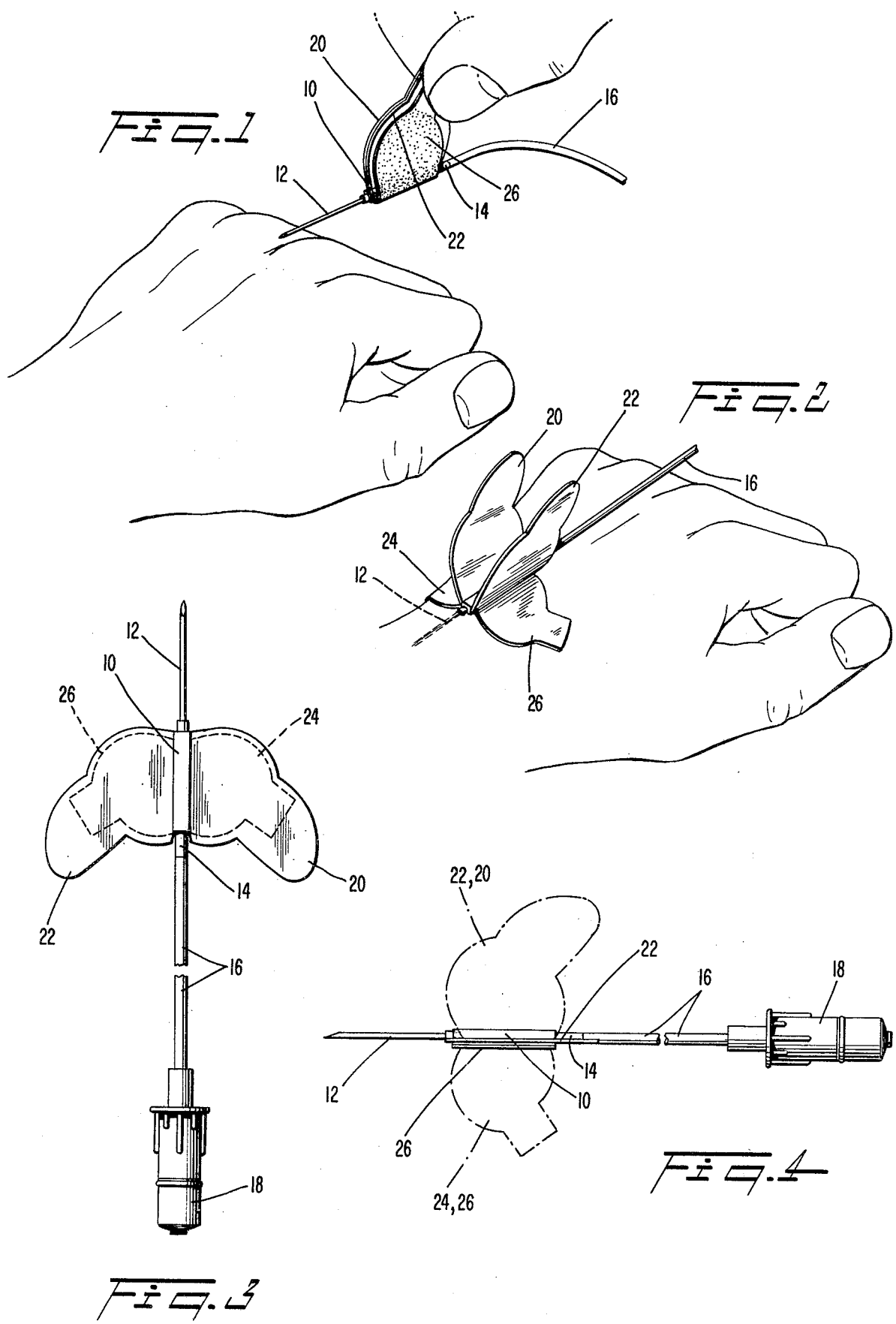

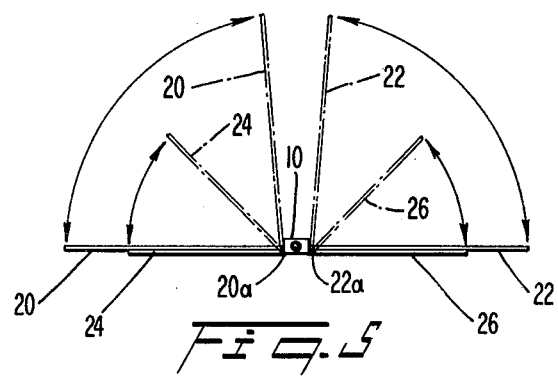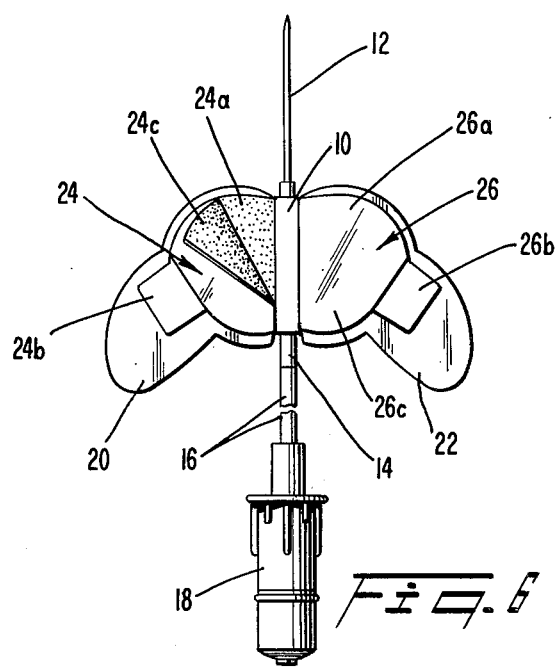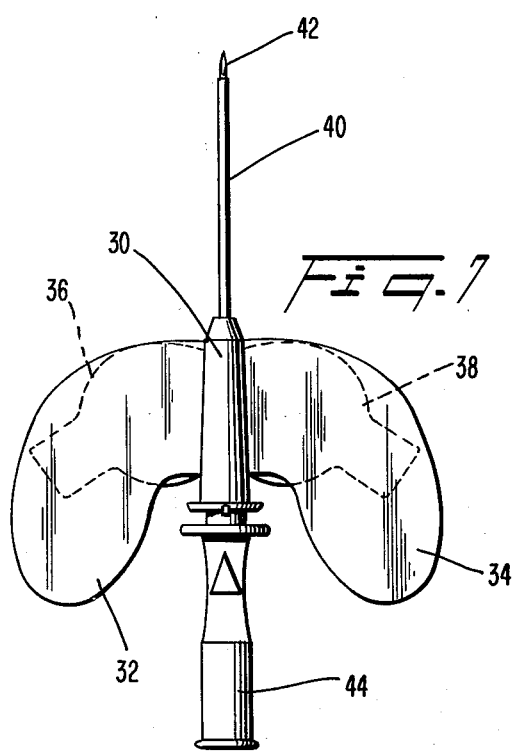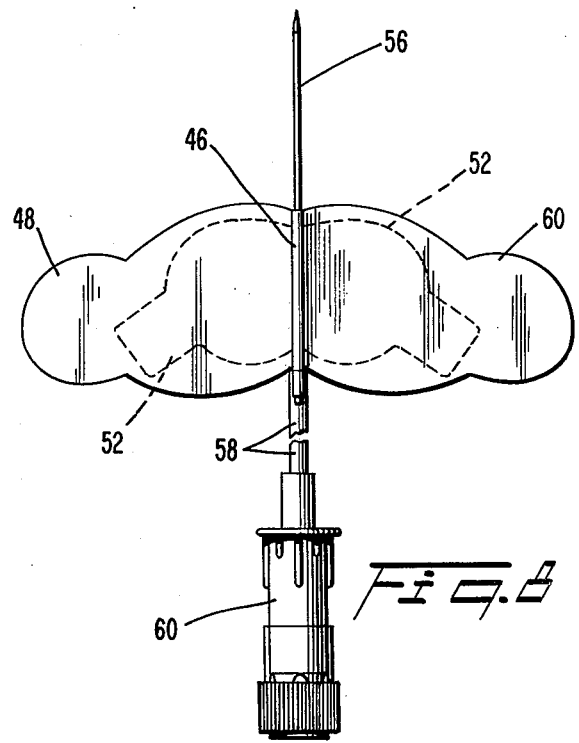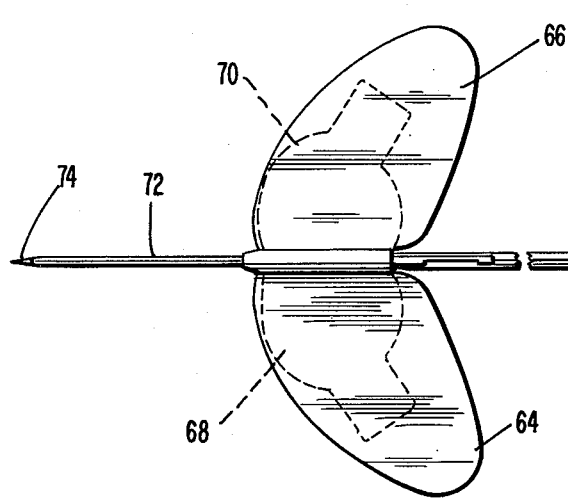

FITTING FOR USE IN PERFORMING A VASCULAR PUNCTURE

BACKGROUND OF THE INVENTION

This invention relates to a fitting for use in performing a vascular puncture, more particularly for obtaining secure stabilization of a needle or catheter to a patient's skin upon entry of the needle or catheter into a blood vessel.

A vascular puncture can be made in many areas of the body such as the forearm, back of the hand, upper arm, ankle or foot by means of a hollow needle or combined cather and stylet with the needle or catheter (after withdrawal of the associated stylet) as the case may be, then remaining attached to the patient for connection, for example, to a source of infusion liquid. It is necessary to stabilize the needle or catheter in relation to the punctured blood vessel to prevent movement of the needle or catheter tending to work it loose or tending to produce undesirable additional blood vessel punctures, which movement can therefore lead to a potential source of infection or irritation to the patient at the point of insertion of the needle or catheter. Stabilization is generally effected by taping the catheter or needle hub and associated tube fittings to the patient's skin in an area adjacent to the point of catheter or needle insertion. It is important to obtain secure stabilization of the inserted catheter or needle and if the stabilizing procedure relies on the individual taping technique of a person performing the vascular puncture, this is a possible source of insecurity of stabilization.

Further, it is desirable that the needle or catheter be stabilized as soon as possible upon insertion into a blood vessel to minimize any risk of undesirable movement thereof relative to the blood vessel.

OBJECTS OF THE INVENTION

It is an object of the invention to provide a fitting which can be used to provide a rapid and standardized technique for securely stabilizing a needle or catheter on a patient's skin subsequent to the formation of a vascular puncture.

It is a further object of the invention to provide the hub of an intravascular needle or catheter with means whereby the needle or catheter can be rapidly and accurately secured on a patient's skin after insertion of the needle or catheter into the blood vessel.

Another object of the invention is to provide an intravascular needle or catheter fitting comprising a hub and stabilizing means integral with the hub which allows the needle or catheter rapidly to be stabilized relative to a blood vessel after insertion thereof into the blood vessel.

A further object of the invention is to provide an intravascular needle or catheter fitting having self-contained stabilizing means enabling a person administering a vascular puncture rapidly and in a simple manner to stabilize the needle or catheter on the patient's skin after forming the puncture.

Still a further object of the invention is to provide a fitting of the kind referred to which is relatively simple and economical to manufacture from readily available materials.

SUMMARY OF THE INVENTION

A fitting for use in forming a vascular puncture is provided which comprises a catheter or needle hub with an associated needle or catheter as the case may be at its one end and means for attaching tubing at the other end and, in accordance with the invention, stabilizing wings extending laterally from the hub. The wings include first and second upper wings of relatively stiff and thick material on opposite sides of the hub, respectively, and third and fourth lower wings of relatively thin light material under the first and second wings. All of the wings can fold up and down independently about the hub and a portion of the undersurface of each of the third and fourth wings carries a contact adhesive normally covered by release paper or the like.

In use, the release paper is stripped from the undersurface of the third and fourth wings and a person administering the vascular puncture folds all four wings up over the hub and grips them together between thumb and finger (for this purpose an outer portion of the undersurfaces of the third and fourth wings is left free of adhesive), the wings thereby affording a convenient manner of gripping the fitting when making a puncture. Immediately upon suitable insertion of the needle or catheter into a blood vessel, the lower wings are released while the grip is still maintained on the upper wings. The lower wings tend to drop and can be lightly dabbed, through their adhesive undersurfaces, onto the skin. This immediately fixes the fitting to the skin and stabilizes it into position. Subsequently the upper wings are folded down onto the skin over the lower wings and can be taped in place more permanently to secure and stabilize the fitting.

Preferably the hub and upper wings are integrally molded in a suitable plastic material such as polyethylene and the lower wings are fused to this unit. The upper wings will generally be of larger area than the lower wings and have a greater thickness. For example, the thickness of the upper wings may be in the range 10 to 100 mils with the thickness of the lower wings being in the range of 5 to 8 mils. Conveniently, to allow bending of the upper wings about the hub, a hinge-type arrangement is provided substantially along the line of junction of these wings with the hub for example by reducing the molding thickness along this line.

The shape of the wings can take any suitable form convenient to facilitate manipulation and subsequent taping down of the fitting and the upper wings may have knurled or otherwise roughened surfaces to improve their gripping characteristics.

BRIEF DESCRIPTION OF THE DRAWINGS

FIGS. 1 and 2 are perspective views illustrating the manner of using one form of intravascular needle fitting made in accordance with the invention;

FIGS. 3, 4, 5 and 6 are respectively a plan, a side elevation, a front view and an underneath plan of the fitting illustrated in FIGS. 1 and 2; and FIGS. 7-9 are plan views of different forms of intravascular fittings made in accordancw with the invention.

DESCRIPTION OF PREFERRED EMBODIMENTS

The needle fitting shown in FIGS. 1-6 comprises a central elongate hub 10 having an associated intravascular needle 12 at its one end and a socket 14 at its other end for tubing 16 and connector 18. The hub is made of suitable plastics material such as polyethylene and has integrally molded therewith a pair of upper laterally extending wings 20 and 22 on opposite sides of the hub respectively. The hub 10 and wings 20, 22 are each preferably formed of a non-porous, hypoallergenic, polyethylene or the like with the wings 20,22 each being approximately 10–100 mils thick and as seen in FIG. 5, each wing has a reduced thickness 20a, 22a along a line corresponding substantially with or adjacent to a line of junction with the hub. This line of reduced thickness provides a hinging effect facilitating upward folding of the wings from their normally flat position shown in FIGS. 3, 5 and 6, and functions in the manner described in detail in U.S. Pat. No. 3,064,648, granted Nov. 20, 1962, the subject matter of which is incorporated herein in its entirety by reference.

Fused to the undersurface of the hub is a member of relatively thin light plastic film or tape, preferably a non-porous, hypoallergenic, polyethylene, providing another pair of laterally extending wings 24 and 26 underneath the first pair of wings 20,22. The tape or film is approximately 5–8 mils in thickness and its undersurface is provided with a contact adhesive, preferably a hypoallergenic, synthetic, acrylic, pressure-sensitive type over portions 24a and 26a. The central portion 28 corresponding substantially to the hub area and outer tab portions 24b and 26b are free of adhesive. Adhesive portions 24a and 26a are covered with a conventional release paper 24c, 26c, as shown in FIG. 6. The wings 24,26 may preferably be a conventional medical or surgical adhesive tape designed for use on human skin such as 3M Brand Medical Tape No. 1517 described in detail in OEM Spec. 1517-1, August 1978 the subject matter of which is incorporated herein in its entirety by reference.

In use, all four wings are folded up over the hub and gripped as shown in FIG. 1, the user gripping the non-adhesive ends or tab portions 24b and 26b of the wings 24 and 26 and the release paper 24c, 26c removed. In this folded condition, the wings 24,26 provide a convenient means for gripping the fitting while performing a vascular puncture and the non-adjesive central portion 28 of the undersurface of the lower wings allows a substantially friction-free sliding of the fitting on a patient's skin while the puncture is being made.

As soon as the needle tip is properly located in a blood vessel, the user releases the lower wings 24,26 while maintaining the grip on the upper wings 20,22. As shown in FIG. 2, the lower wings tend to drop onto the patient's skin and can be lightly dabbed down so that the contact adhesive provides immediate stabilization of the fitting. For more permanent stabilization, the upper wings are folded down over the lower wings and taped in place.

As shown in FIGS. 7–9 the wings can be made in numerous shapes and can be applied to a variety of different needle or catheter fittings. In each case, the lower wings are generally of smaller area than the upper wings and it will be understood that in other respects the construction shown in the later figures are similar to that described with reference to the FIGS. 1–6 insofar as the wing thickness, folding ability and adhesive nature of portions of the lower wings are concerned. Thus FIG. 7 shows the invention as applied to a catheter fitting having a hub 30, with integrally molded upper wings 32 and 34, lower wings 36 and 38, catheter 40, withdrawable stylet 42 and stylet hub 44. FIG. 8 shows another needle fitting having a hub 46, upper wings 48 and 50, lower wings 52 and 54, needle 56, tubing 58 and connector 60. Another form of catheter fitting is shown in FIG. 9 comprising a catheter hub 62, integrally molded upper wings 64 and 66, lower wings 68 and 70, catheter 72, stylet 74, connector 76 and stylet hub 78. It will be appreciated that the manner of using and stabilizing the fittings illustrated in FIGS. 7-9 is similar to that described on relation to FIGS. 1-6.

It should be noted that the base of the hub can in all cases be made flat or at any suitable angle longitudinally of the fitting to establish the correct angle relative to a blood vessel for the associated catheter or needle as the case may be when the fitting is in position on a patient's skin.

From the foregoing description, it can be seen that the instant invention provides a fitting for use in intravascular puncture procedures which enables a needle or catheter to be rapidly and securely stabilized on a patient's skin immediately upon insertion of the needle or catheter into the blood vessel. The device is relatively simple to use and can be readily and economically manufactured from readily disposable materials.

Further, while preferred embodiments of the invention have been described herein in detail, the invention is not limited to the particular features of the embodiments and numerous modifications can be made within the scope of the appended claims. For example, in certain applications, sufficient initial stabilization of the device may be obtained with only a single lower wing under one of the upper wings rather than a lower wing under each of the upper wings as described. The single lower wing would of course still have contact adhesive on part of its undersurface. Also, a device in accordance with the invention can be produced by applying lower wings of the type described to an existing fitting having a hub with a single set of laterally extending wings.

By providing the relatively lightweight and highly flexible lower wings the fitting can be quickly and readily secured to a portion of the patient's body of any configuration. The conventional upper wings, due to their relative thickness and inflexibility, accommodate themselves to selected body surfaces poorly, cause inadequate stabilization and insecure attachment of the fitting resulting in possible trauma or irritation to the puncture site. The ability to grip and fold both sets of wings simultaneously without engaging an adhesive surface, to slide the hub portion over the skin to produce the venipuncture, and then to easily and efficiently cause immediate and positive securement of the fitting produces obvious advantages, both from the standpoint of the patient and the nurse.

What is claimed is:

1. A fitting for use in forming a vascular puncture comprising an elongate hub having a longitudinal axis, a blood vessel-entering element extending axially from one end of said hub, tubing attachment means at the other end of said hub and means for stabilizing the fitting on a patient's skin upon insertion of said blood vessel-entering element into a blood vessel, said stabilizing means including first and second substantially laminar wings extending laterally from said hub on opposite sides of said axis respectively, a third substantially laminar wing extending laterally from said hub under one of said first and second wings, each of said first, second and third wings being capable of independent flexing movements about said hub and said third wing having an undersurface with contact adhesive means covering a portion of said surface, wherein said undersurface of said third wing comprises a hub-covering portion, an outer gripping portion and a central portion between said hub-covering portion and said gripping portion and wherein said contact adhesive is provided on said central portion.

2. A fitting for use in performing a vascular puncture comprising an elongate hub having a longitudinal axis, a blood vessel-entering element extending axially from one end of said hub, and tubing attachment means at the other end of said hub, said fitting further comprising:

preliminary stabilizing means for providing positional stability of said fitting on a patient's skin immediately after insertion of said blood vessel-entering element into that patient's blood vessel, said preliminary stabilizing means comprising a first substantially laminar wing-like member having top and bottom surfaces and extending laterally from said hub, said first wing-like member being capable of flexure about said longitudinal axis and having a coating of adhesive material on at least a portion of its bottom side; and further means for gripping said fitting during vascular insertion of said element and stabilizing the element on the patient's skin subsequent to stabilization by said preliminary stabilizing means, said further means comprising second and third substantially laminar wing-like members having top and bottom sides and normally extending laterally from said hub on opposite sides, respectively, of said axis, said second wing-like member normally extending over said first wing-like member, said second and third wing-like members being flexible to permit their independent flexure about said hub such that said second and third wing-like members can be flexed to bring their top sides toward one another to permit said first and second wing-like members to serve as a handle during vascular insertion of said element.

3. The fitting according to claim 2, wherein said preliminary stabilizing means further comprises a fourth substantially laminar wing-like member having top and bottom sides and extending laterally from said hub beneath said third wing-like member, said fourth wing-like member being capable of flexure about said hub independently of said first, second and third wing-like members and having a coating of adhesive material on at least a portion of its bottom side.

4. The fitting as defined in claim 3, wherein said first and fourth wing-like members are substantially thinner than said second and third wing-like members.

5. The fitting according to claim 2, wherein the bottom surface of said first wing-like member comprises a hub-covering portion, an outer gripping portion and a central portion between said hub-covering portion and said gripping portion, and wherein said adhesive material is provided on said central portion.

6. The fitting as defined in claim 2, wherein said first wing-like member has a smaller area than said second wing-like member and is positioned relative to the hub so as to fit within the perimeter of said second wing-like member when viewed in plan.

7. The fitting as defined in claim 2, further comprising means a defining a hinge line between each of said second and third wing-like members and said hub.

8. The fitting as defined in claim 2, wherein said hub and said second and third wing-like members comprise an integral molding in plastics material.

9. The fitting as defined in claim 8, further comprising means fusing said first wing-like member to said integral molding.

10. The fitting according to claim 9, wherein said first wing-like member is plastic web having a thickness in the range of 5 to 8 mils.

11. The fitting according to claim 8, wherein said second and third wing-like members each have a thickness in the range of 10 to 100 mils.

* * * * *